United States Patent
Legloahec et al.

(10) Patent No.: US 6,225,475 B1
(45) Date of Patent: May 1, 2001

(54) ENHANCED PRODUCTION OF HYDROCARBYL ANHYDRIDES

(75) Inventors: Valerie N. Legloahec; Patrick C. Hu, both of Baton Rouge, LA (US)

(73) Assignee: Albemarle Corporation, Richmond, VA (US)

( * ) Notice: Subject to any disclaimer, the term of this patent is extended or adjusted under 35 U.S.C. 154(b) by 0 days.

(21) Appl. No.: 09/641,534

(22) Filed: Aug. 18, 2000

(51) Int. Cl.⁷ .................... C07D 307/60; C07D 307/77
(52) U.S. Cl. ............................ 549/233; 549/240
(58) Field of Search ..................... 549/233, 240

(56) References Cited

U.S. PATENT DOCUMENTS 5,770,744 * 6/1998 Darsow ................. 549/233

OTHER PUBLICATIONS

Block, Seymour, S., "Disinfection, Sterilization, and Preservation" Fourth Edition, Chapter 13, "Quaternary Ammonium Antimicrobial Compounds", Lea & Febiger, 1991, pp. 225–255.

* cited by examiner

Primary Examiner—Joseph K. McKane
Assistant Examiner—Joseph Murray
(74) Attorney, Agent, or Firm—Philip M. Pippenger

(57) ABSTRACT

To form a mixture of anhydrides suitable for use as a curing agent for epoxy resins, a mixture formed from maleic anhydride and a liquid monoolefin is heated to produce a reaction mass containing a liquid phase comprised of alkenyl succinic anhydride, maleic anhydride, and monoolefin. Then a conjugated diene hydrocarbon is mixed with this reaction mass and the temperature of the resultant mixture is such as to form a reaction mass comprising tetrahydrophthalic anhydride and/or alkyl-substituted tetrahydrophthalic anhydride and alkenyl succinic anhydride.

31 Claims, No Drawings

ENHANCED PRODUCTION OF HYDROCARBYL ANHYDRIDES

TECHNICAL FIELD

This invention relates to a new way of producing mixtures of hydrocarbyl anhydrides which can be used, for example, as curing agents for epoxy resins.

BACKGROUND

Aliphatic and cycloaliphatic anhydrides such as commercial grades of dodecenyl succinic anhydride (DDSA) and of methyl tetrahydrophthalic anhydride (MTHPA) are used as curing agents in the production of epoxy resins. In some cases these aliphatic and cycloaliphatic anhydrides are used individually and in some cases they are used in combination with each other. If DDSA is used by itself, the resultant epoxy resin has a relatively low glass transition temperature (in the order of about 80° C.). On the other hand, use of MTHPA produces epoxy resins having higher glass transition temperatures (in the order of about 140° C.). Therefore, mixtures of DDSA and MTHPA are used to provide epoxy resins having physical properties required for use under various actual service conditions, such as, for example, desired glass transition temperatures, suitable polymer modulus, and the like.

Heretofore, the desired mixture of DDSA and MTHPA has been produced either by purchasing the individual products and mixing them together at the polymerization site prior to conducting the polymerization or by purchasing a preformed mixture of the DDSA and MTHPA from the supplier. So far as is known, the supplier forms such preformed mixtures from DDSA and MTHPA which have been produced in separate chemical operations.

Typically, the alkenyl succinic anhydrides are formed by reacting a branched olefin such as propylene tetramer with maleic anhydride. During the reaction it is desirable to consume the majority, if not all, of the maleic anhydride so that little if any unreacted maleic anhydride will need to be recycled. One way of improving the consumption of the maleic anhydride during the reaction is to perform the reaction at an elevated temperature. In the case of DDSA production temperatures as high as 250° C. are required in order to achieve sufficient reaction kinetics (rapidity of reaction). Unfortunately at such temperatures, side reactions may occur even though short reaction times are used. Such side reactions can and often do result in formation of products having unattractive dark coloration. From a commercial standpoint, it would be advantageous to provide a product possessing improved color characteristics.

A need thus exists for a method in which the DDSA can be produced rapidly and without appreciable color development during its synthesis thereby obviating the need for use of purification procedures such as distillation or decolorization.

The conventional method for producing commercial grade MTHPA involves the reaction of maleic anhydride with isoprene, piperylene, or butadiene, or a mixture containing these dienes. The resultant product of this Diels-Alder reaction is a solid at room temperature. A liquid form of this product is highly desired in the marketplace. To fulfill this requirement, it has been the practice heretofore to subject the product either to hydrogenation whereby the double bond is saturated by hydrogen, or to isomerize the product usually in the presence of a catalyst. Both such operations are not only time consuming, but add substantial capital and processing costs to the operation.

A need thus exists for a way of producing a liquid product containing MTHPA without requiring recourse to hydrogenation or isomerization.

SUMMARY OF THE INVENTION

Pursuant to this invention, both of the foregoing needs are fulfilled in a single unitary operation.

Provided by this invention in one of its embodiments is a process which comprises:

a) heating a mixture formed from maleic anhydride and at least one liquid monoolefin to produce a reaction mass containing a liquid phase, such liquid phase comprising at least one alkenyl succinic anhydride, maleic anhydride, and at least one monoolefin; and b) mixing at least one conjugated diene hydrocarbon with reaction mass from a) and having the temperature of the resultant mixture sufficient to form a reaction mass comprising at least tetrahydrophthalic anhydride and/or alkyl-substituted tetrahydrophthalic anhydride and at least one alkenyl succinic anhydride.

The resulting product is readily recovered in suitable form for commercial uses, even commercial uses requiring light-colored materials. For example, product recovery can be accomplished by flashing or vaporizing the residual amounts of unreacted starting materials, mostly olefin, from the reaction mixture. Thus, no hydrogenation or isomerization and no product decolorization is required—all such operations can be eliminated in their entirety. Moreover, unlike present commercial operations wherein two separate reactions are used in order to prepare DDSA on the one hand and MTHPA on the other, this invention has made it possible to produce both products as a liquid mixture in a unitary operation. And from an operational standpoint, the processes of this invention enable significant increases in plant throughput.

It is therefore preferable to recover the residual amount of unreacted starting materials from the reaction mass formed in b), most preferably by distillation. It is also preferred to recycle at least a portion of the recovered residual amount of unreacted starting materials as a part of the feed to a subsequent reaction. If more than about 10 wt % of the recovered residual amount of unreacted starting materials is composed of diene hydrocarbon(s), the portion used in the recycle will usually be, and preferably is, fed to step b). On the other hand, when less than about 10 wt % of the recovered residual amount of unreacted starting materials is composed of diene hydrocarbon(s), it is usually preferable to recycle at least a portion of this residual amount as feed to a). However, common sense should of course be used when deciding to which step the recycled material(s) should fed.

Another embodiment of this invention is a process which comprises:

a) heating a mixture formed from maleic anhydride and a stoichiometric excess of at least one branched olefin and/or internal linear olefin having in the range of about 6 to about 18 carbon atoms in the molecule at a temperature in the range of about 180 to about 280° C. to form a reaction mass containing a liquid phase, such liquid phase comprising at least one alkenyl succinic anhydride in which the alkenyl group contains in the range of about 6 to about 18 carbon atoms, maleic anhydride, and at least one olefin containing in the range of about 6 to about 18 carbon atoms in the molecule; and b) mixing at least one conjugated diene hydrocarbon having in the range of 4 to about 12 carbon atoms with reaction mass from a) and having the temperature of the resultant mixture in the range of about 20 to about 180° C. to form a reaction mass comprising at least tetrahydrophthalic anhydride and/or alkyl-substituted tetrahydrophthalic anhydride, and at least one alkenyl succinic anhydride.

Still another embodiment of this invention is a process which comprises:

a) heating a mixture formed from maleic anhydride and a stoichiometric excess of olefin consisting essentially of at least one $C_{12}$ branched olefin and/or at least one internal linear olefin at a temperature in the range of about 180 to about 280° C. to form a reaction mass containing a liquid phase, the liquid phase comprising at least one $C_{12}$ alkenyl succinic anhydride, residual maleic anhydride, and $C_{12}$ branched and/or internal linear olefin; and b) mixing with reaction mass from a) at least one conjugated diene hydrocarbon having in the range of 4 to about 6 carbon atoms in an amount at least stoichiometrically equivalent to the amount of residual maleic anhydride present in the reaction mass from a), and thereafter having the temperature of the resultant mixture in the range of about 40 to about 150° C. to form a reaction mass comprising at least tetrahydrophthalic anhydride and/or alkyl-substituted tetrahydrophthalic anhydride, and at least one $C_{12}$ alkenyl succinic anhydride.

In each of the embodiments described in the two immediately preceding paragraphs, the reaction mass formed in b) can then be subjected to any of a variety of workup procedures in order to separate and recover unreacted starting materials for recycle, and also to enable recovery of a purified product comprising at least about 95 wt % of the combination of tetrahydrophthalic anhydride and/or alkyl-substituted tetrahydrophthalic anhydride, and at least one alkenyl succinic anhydride. Additionally such embodiments are preferably carried out in the same reaction vessel without removing the reaction mass of a) from the reaction vessel.

Other embodiments and features of this invention will be still further apparent from the ensuing description and appended claims.

FURTHER DETAILED DESCRIPTION

Step a)—The Thermal Ene Reaction

In the first stage of the processes of this invention, a thermal ene reaction is performed between a liquid olefin and maleic anhydride. The mole ratio of olefin to maleic anhydride should be at least about 0.5, and since the olefin is a liquid, there is no mandatory upper limit other than reactor volume. However, in most operations the mole ratio will not exceed about 3.0. Ratios above this only add to the volume of raw materials that need to be recovered for recycle. Typically the mole ratio of olefin to maleic anhydride fed to the reaction will be in the range of about 0.65 to about 2.5. Preferably the mole ratio of olefin to maleic anhydride is in the range of about 1.0 to about 2.0.

The reactants in the ene reaction can be added concurrently and/or in any sequence to the reaction vessel. Thus, the olefin can be added to the maleic anhydride, the maleic anhydride can be added to the olefin, and/or the olefin and the maleic anhydride can be cofed to the reaction vessel. Preferably, the olefin is charged to the reactor and thereafter the maleic anhydride is introduced into the olefin. It is desirable to add the maleic anhydride in molten form to the olefin while agitating and heating up the resultant mixture as this facilitates the formation of a homogeneous liquid phase. Preferably, the olefin is preheated to a temperature in the range of about 60 to about 250° C., and more preferably in the range of about 180 to about 250° C., before initiating the feed of the molten maleic anhydride to the olefin. The resultant mixture is subjected to agitation to ensure intimate contact between these reactants. However, when the maleic anhydride is added in solid form to the olefin, it is desirable to heat the resultant mixture to a temperature at which the maleic anhydride melts, and thereupon to initiate agitation.

In a cofeed operation the maleic anhydride can be introduced to the reactor either in solid or molten form depending upon whether the reactor is already closed or is open during the addition and is sealed thereafter. If fed to an already closed reactor, it is desirable to preheat at least the maleic anhydride and more preferably both reactants to a temperature below the ene reaction temperature before introducing them into the reactor and to maintain the temperature of the already closed reactor at the selected ene reaction temperature. On the other hand when cofeeding to an open reactor, the maleic anhydride can either be in solid or molten form but below the ene reaction temperature, preferably the latter, and the olefin can be added either at room temperature or as preheated olefin at a temperature below its boiling temperature. After the reactants have been introduced, the open reactor is sealed and the contents are thereupon heated to the selected ene reaction temperature.

In conducting the ene reaction itself, the presence of air should be avoided. Thus, an inert gas such as nitrogen is typically used to flush the reaction zone before the reactants are brought to the ene reaction temperature.

Advantages are obtained by charging the maleic anhydride to the reaction vessel in molten condition. First of all, and as noted above, this facilitates the formation of a homogeneous liquid phase. Secondly, the molten maleic anhydride can be maintained under an inert atmosphere, such as nitrogen, and when the feeding takes place, the inert gas can accompany the molten maleic anhydride being charged to the reaction vessel. This in turn minimizes exposure of the hot maleic anhydride to the air.

The ene reaction is carried out in such a way as to produce a liquid reaction mixture composed of at least one alkenyl succinic anhydride, maleic anhydride, and at least one monoolefin. One way of accomplishing this objective is to perform the reaction at a temperature in the range of about 180 to about 280° C., and preferably in the range of about 200 to about 250° C., until the desired conversion of maleic anhydride is achieved. Conversions in the range of 50 to 95 mole % are typical. In designing a particular operation procedure, it is desirable to conduct one or more pilot operations in which the reaction is conducted at a selected reaction temperature and is monitored by means of GC in order to determine the time required to achieve particular mole % conversions of the maleic anhydride at the selected temperature. With the knowledge of the reaction kinetics obtained in this manner, it is possible to conduct a full scale operation at a preselected reaction temperature by suitable selection of the reaction time to achieve the desired mole % conversion without monitoring the reaction. Generally speaking, the longer the time at a given temperature in the range of 180 to 280° C., the higher the mole % conversion of maleic anhydride.

Olefins used in the ene reaction of the present invention will typically be composed predominately of branched $C_{12}$ olefins, typically propylene tetramer. Alternatively, individual linear internal olefins or mixtures of linear internal olefins having in the range of about 6 to about 18 carbon atoms, and preferably in the range of about 8 to about 14 carbon atoms, in the molecule can be used. Such linear internal olefins will form products similar to DDSA having alkyl substituents in the range of about 6 to about 18 carbon atoms. The configuration of such alkyl substituents will of course differ from that provided by propylene tetramer. Products formed using such linear internal olefins as well as products formed using mixtures of propylene tetramer and one or more such linear internal olefins, are deemed suitable for preparing ene reaction products useful in the manufacture of epoxy resins.

When the ene reaction of a) is conducted using maleic anhydride and at least one $C_{12}$ branched olefin and/or at least one internal linear olefin, the reaction is preferably carried out at a temperature in the range of about 180 to about 280° C.

Whatever the manner and conditions used in conducting the thermal ene reaction, the reaction product will contain a mixture of one or more alkenyl succinic anhydrides, unreacted maleic anhydride, and in most cases, unreacted olefin.

Step b)—The Diels-Alder Reaction

This step involves mixing at least one conjugated diene with the product formed in Step a) so that a Diels-Alder reaction can take place between the unreacted maleic anhydride and the conjugated diene. This reaction, of course, will take place in the presence of the alkenyl succinic anhydride (s) carried over from Step a).

Conjugated diene hydrocarbons suitable for use in the practice of this invention can be in the form of a one or more pure dienes or in the form of a mixture of one or more dienes additionally containing one or more other hydrocarbon components, notably paraffinic hydrocarbons. Typically, the diene hydrocarbon(s) used in the process will contain in the range of about 4 to about 12 carbon atoms. Preferably, the conjugated diene hydrocarbon contains in the range of about 4 to about 8 carbon atoms in the molecule. Use of butadiene, isoprene, or piperylene, or a mixture of at least two of them is particularly preferred. Mixtures of such dienes in association with paraffinic hydrocarbons are available as articles of commerce at relatively low cost and thus are especially preferred for use in the process.

In carrying out the Diels-Alder reaction, several alternative procedures can be used. In one case, the reaction mass formed in a) is cooled or allowed to cool to a temperature in the range of about 20 to about 180° C., conjugated diene hydrocarbon is mixed with the so-cooled reaction mass of a), and the temperature in b) is maintained in the range of about 40 to about 150° C. In another such procedure the reaction mass formed in a) is cooled or allowed to cool to a temperature in the range of about 50 to about 180° C., and the conjugated diene hydrocarbon is mixed with the reaction mass of a) while such reaction mass is at a temperature of at least about 50° C., so that the reaction mass of) is formed without applying additional heat while conducting b). Still another variant in procedure involves cooling or allowing the reaction mass formed in a) to cool to a temperature in the range of about 20 to about 80° C., mixing the conjugated diene hydrocarbon with the so-cooled reaction mass of a), and heating the resultant mixture to a temperature in the range of about 50 to about 150° C. In each of these procedures it is desirable to separate the unreacted starting materials from the reaction mass formed in b), and to use at least a portion of the recovered unreacted starting materials as part of the feed in a subsequent reaction. Thus irrespective of the procedure used, this invention makes it possible to form and recover a purified mixture of at least tetrahydrophthalic anhydride and/or alkyl-substituted tetrahydrophthalic anhydride, and at least one alkenyl succinic anhydride. The proportion of the liquid alkenyl succillic anhydride to the normally solid tetrahydrophthalic anhydride and/or alkyl-substituted tetrahdyrophthalic anhydride in the purified anhydride mixture should be sufficient to produce a liquid product. Such liquid products are very desirable as articles of commerce. Thus, in any situation where the appropriate proportions of the reactants to produce such a liquid mixture have not already been established, it is desirable to perform a few pilot experiments in order to identify a suitable set of proportions which will produce the desired liquid product. In the case of an anhydride product mixture formed from a $C_{12}$ monoolefin and a diene hydrocarbon or mixture of diene hydrocarbons having 4 to 5 carbon atoms, the weight ratio of the $C_{12}$ alkenyl succinic anhydride to the tetrahydrophthalic anhydride and/or methyl-substituted tetrahydrophthalic anhydride in the product should be greater than 1:1 so that the product is a liquid, for example at 20° C.

A further preferred embodiment of this invention is to conduct a) and b) in the same reaction vessel without removing the reaction mass of a) from the reaction vessel. A particularly preferred embodiment comprises distilling unreacted and/or residual starting materials from the reaction mass formed in b) to form a purified mixture of at least tetrahydrophthalic anhydride and/or alkyl-substituted tetrahydrophthalic anhydride, and at least one alkenyl succinic anhydride; and conducting at least a) and b) in the same reaction vessel without removing the reaction mass of a) from said reaction vessel.

If desired, the process of this invention can be carried out by conducting Step a) to produce a reaction product mixture containing an amount of residual maleic anhydride that is insufficient for step b), and then to conduct Step b) by addition of the diene and fresh maleic anhydride, e.g., in an amount that at least makes up the deficiency of residual maleic anhydride remaining after Step a). This mode of operation can be used as a way of ensuring that the reactants are present at all times in the proper proportions. In addition, it enables more efficient use of reactor volume in Step a), since less volume is taken up by the maleic anhydride present in Step a).

Usually the diene and, if used, make-up maleic anhydride, will simply be added to the reaction product from Step a) in the same or a different reactor. However, if desired, the reaction product from Step a) with or without added maleic anhydride can be added to the diene, or such materials can be concurrently fed individually and/or in one or more subcombinations to a second reactor.

Another variant in procedure involves carrying out Step a) in such a way as to consume all of the maleic anhydride in Step a), and to conduct Step b) by the addition of fresh maleic anhydride along with the diene. In this case, the Diels-Alder reaction is performed in the presence of alkenyl succinic anhydride produced in Step a). This process is not preferred however, because at modest reaction temperatures, which avoid production of an undesirable dark alkenyl succinic anhydride product, the thermal ene reaction is exceedingly slow. On the other hand, if the thermal ene reaction is carried out at still higher reaction temperatures in order to increase reaction rate, the alkenyl succinic anhydride product of Step a) will also be dark in color.

The following Examples are presented to illustrate the practice and features of the invention. These Examples are not intended to limit, do not limit, and should not be construed as limiting the scope of this invention. In these Examples, DDSA denotes dodecenyl succinic anhydride, THPA denotes tetrahydrophthalic anhydride, and MTHPA denotes methyltetrahydrophthalic anhydride.

EXAMPLE 1

Preparation of DDSA/MTHPA Blend

The raw materials used in this operation were propylene tetramer supplied by Sunoco or Imperial Oil Esso and isoprene (99.5% pure) was supplied by Goodyear. A 1 L-nitrogen-dried stainless steel Parr reactor, fitted with mechanical stirrer, cooling coils, sampling dip-leg, vent, rupture disk, a pressure sensor, a thermocouple well, and a nitrogen inlet tube was charged with maleic anhydride (86.5 g, 1 eq.) and propylene tetramer (370 g, 2.5 eq.). The vessel was then bolted to the reactor frame and the reaction mixture was purged with nitrogen for 5–10 minutes. The mixture was then heated at 200° C. while stirring at 900 rpm, this stirring being initiated when the reaction temperature had reached 55–60° C., the temperature at which maleic anhydride melts. The pressure built-up in the reactor was monitored with time and temperature (Pmax=39 psi). Sampling was performed during the course of the reaction until the desired conversion (followed by GC) with respect to maleic anhydride was achieved. After the reaction was conducted for 4 hours the reaction mass was cooled to 80° C. by means of external cooling coils on the reactor mantel. Then isoprene (33 g) was introduced through the inlet tube into the reaction mixture. After the isoprene addition, stirring was resumed and the reaction mixture was heated at 100° C. for one hour. The GC analysis showed that no residual maleic anhydride remained in the reaction mixture. The hot reaction mixture was then cooled and the reactor was discharged to a nitrogen-padded sample bottle while venting it with nitrogen. Unreacted starting materials (mostly residual olefin and isoprene) were stripped off under reduced pressure using Kügelrohr equipment. Analysis of the purified light yellow liquid product showed that the product was composed of 83 wt % of DDSA and 17 wt % of MTHPA.

EXAMPLE 2

Preparation of DDSA/MTHPA Blend

The procedure of Example 1 was successfully repeated under the same conditions except that the maleic anhydride was fed in molten form instead of feeding it as as solid.

EXAMPLE 3

Preparation of DDSA/MTHPA Blend

A 1 L-nitrogen-dried stainless steel Parr reactor, equipped with a mechanical stirrer, a thermocouple well and a nitrogen inlet tube, was charged with propylene tetramer (370 g, 2.5 eq.). The vessel was then bolted to the reactor frame, and the reaction mixture was purged with nitrogen for 10–15 minutes. The mixture was heated at 180° C. while stirring at 900 rpm. Then, molten maleic anhydride (86.5 g, 1 eq.) was introduced through the inlet tube. The reaction mixture was then heated at 200° C. until the desired conversion with respect to malcic anhydride was achieved. Then, the same experimental procedure as set forth in Example 1 was followed.

EXAMPLE 4

Preparation of DDSA/THPA Blend

A 5 L-nitrogen-dried Büchi reactor, fitted with a mechanical stirrer, a sampling dip-leg, a vent, a rupture disk, a pressure sensor, a thermocouple well and a nitrogen inlet tube, was charged with propylene tetramer (2000 g, 1.75 eq.) and maleic anhydride (677 g, 1.0 eq.). The maleic anhydride was added as a solid (crushed briquettes from Aldrich) at room temperature. The reactor was then sealed and flushed with nitrogen for 5–10 min (5 psi of nitrogen was left in the reactor) before heat was applied. The mixture was heated up to 225–230° C. while stirring at 1000 rpm, the stirring being initiated when the reaction temperature had reached 55–60° C. The pressure built-up in the reactor was monitored with time and temperature (Pmax=54 psi). Sampling was performed during the course of the reaction until the desired conversion (followed by GC) with respect to maleic anhydride was achieved. After 4.5 hours of reaction, the reaction mass was cooled to 95° C. Butadiene (162 g; supplied by Matheson) was fed into the cooled reaction mixture through the inlet tube. After the butadiene addition, stirring was resumed without applying any additional heat. After two hours of reaction GC analysis showed that the maleic anhydride had been completely reacted. The contents of the reactor at a temperature of 55° C. were then discharged to a nitrogen-padded sample bottle while venting it with nitrogen. Analysis of the crude reaction mixture showed that it contained 54.96 wt % of DDSA, 5.68 wt % of THPA, 39.35 wt % of propylene tetramer and 0.01 wt % of maleic anhydride. Thus the weight ratio of the DDSA to THPA in this crude product was approximately 9.7:1. Unreacted starting materials (mostly residual olefin) were removed by flash distillation under reduced pressure using Kügelrohr equipment at an applied vacuum of 14.8 mmHg. After this purification, the product was a light yellow colored liquid.

As noted above, the preferred products formed by the process technology of this invention are those that are liquids at ambient room temperatures. To assist in targeting particular products that meet this criterion, blends were made up using different proportions of (a) DDSA and THPA, (b) DDSA and MTHPA, and (c) DDSA, THPA, and MTHPA to assess their physical states at room temperature. The results are summarized in the Table.

TABLE

Physical States of Mixtures at Room Temperature

| DDSA, wt % | MTHPA, wt % | THPA, wt % | Physical State |
|---|---|---|---|
| 90 | 0 | 10 | Liquid |
| 85 | 0 | 15 | Solid |
| 50 | 50 | 0 | Solid |
| 55 | 45 | 0 | Liquid |
| 58.5 | 31.5 | 10 | Liquid |
| 72.5 | 22.5 | 5 | Liquid |
| 63 | 27 | 10 | Liquid |
| 54 | 36 | 10 | Liquid |

It is to be understood that the components or reactants referred to anywhere in the specification or claims hereof, whether referred to in the singular or plural, are identified as they exist prior to coming into contact with another substance referred to by chemical name or chemical type. Also, even though the claims hereinafter may refer to substances or components in the present tense ("comprises", "is", etc.), the reference is to the substance, component or ingredient as it existed at the time just before it was first contacted, blended or mixed with one or more other substances or components in accordance with the present disclosure.

This invention is susceptible to considerable variation in its practice. Therefore the foregoing description is not intended to limit, and should not be construed as limiting, the invention to the particular exemplifications presented hereinabove. Rather, what is intended to be covered is as set forth in the ensuing claims and the equivalents thereof permitted as a matter of law.

That which is claimed is:

1. A process which comprises:
   a) heating a mixture formed from maleic anhydride and at least one liquid monoolefin to produce a reaction mass containing a liquid phase, said liquid phase comprising at least one alkenyl succinic anhydride, maleic anhydride, and at least one monoolefin; and
   b) mixing at least one conjugated diene hydrocarbon with reaction mass from a) and having the temperature of the resultant mixture sufficient to form a reaction mass comprising at least tetrahydrophthalic anhydride and/or alkyl-substituted tetrahydrophthalic anhydride and at least one alkenyl succinic anhydride.

2. A process according to claim 1 further comprising recovering the residual amount of unreacted starting materials from the reaction mass formed in b).

3. A process according to claim 2 wherein at least a portion of the recovered residual amount of unreacted starting materials is recycled as a part of the feed to a subsequent reaction.

4. A process according to claim 2 wherein said residual amount of unreacted starting materials is recovered by distillation.

5. A process according to claim 4 wherein at least a portion of the recovered residual amount of unreacted starting materials is recycled as a part of the feed to a subsequent reaction.

6. A process according to any of claims 1–5 wherein the reaction mass formed in a) is cooled or allowed to cool to a temperature in the range of about 20 to about 180° C., wherein said conjugated diene hydrocarbon is mixed with the so-cooled reaction mass of a), and wherein temperature in b) is in the range of about 40 to about 150° C.

7. A process according to any of claims 1–5 wherein the reaction mass formed in a) is cooled or allowed to cool to a temperature in the range of about 50 to about 180° C., and wherein said conjugated diene hydrocarbon is mixed with the reaction mass of a) while said reaction mass is at a temperature of at least about 50° C., so that the reaction mass of b) is formed without applying additional heat while conducting b).

8. A process according to any of claims 1–5 wherein the reaction mass formed in a) is cooled or allowed to cool to a temperature in the range of about 20 to about 80° C., wherein said conjugated diene hydrocarbon is mixed with the so-cooled reaction mass of a), and wherein the resultant mixture is heated to a temperature in the range of about 50 to about 150° C.

9. A process according to claim 1 wherein the mole ratio of the monoolefin to maleic anhydride fed to the reaction is at least about 0.65:1 to about 2.5:1.

10. A process according to claim 1 wherein the mole ratio of the monoolefin to maleic anhydride fed to the reaction is at least about 1:1 to about 2:1.

11. A process according to any of claims 1–5 wherein at least a) and b) are conducted in the same reaction vessel without removing the reaction mass of a) from said reaction vessel.

12. A process according to claim 1 wherein the mixture formed from maleic anhydride and liquid monoolefin in a) is formed by adding molten maleic anhydride to said monoolefin.

13. A process according to claim 1 wherein in b) maleic anhydride is added to the mixture from which said reaction mass of b) is formed.

14. A process which comprises:
    a) heating a mixture formed from maleic anhydride and a stoichiometric excess of at least one branched olefin and/or internal linear olefin having in the range of about 6 to about 18 carbon atoms in the molecule at a temperature in the range of about 180 to about 280° C. to form a reaction mass containing a liquid phase, said liquid phase comprising (i) at least one alkenyl succinic anhydride in which the alkenyl group contains in the range of about 6 to about 18 carbon atoms, (ii) maleic anhydride, and (iii) at least one olefin containing in the range of about 6 to about 18 carbon atoms in the molecule; and
    b) mixing at least one conjugated diene hydrocarbon having in the range of 4 to about 12 carbon atoms with reaction mass from a) and having the temperature of the resultant mixture in the range of about 20 to about 180° C. to form a reaction mass comprising at least tetrahydrophthalic anhydride and/or alkyl-substituted tetrahydrophthalic anhydride, and at least one alkenyl succinic anhydride.

15. A process according to claim 14 further comprising recovering from the reaction mass of b), a product consisting essentially of tetrahydrophthalic anhydride and/or alkyl-substituted tetrahydrophthalic anhydride, and at least one alkenyl succinic anhydride.

16. A process according to claim 14 wherein the reaction mass formed in a) is cooled or allowed to cool to a temperature in the range of about 20 to about 180° C., wherein said conjugated diene hydrocarbon is mixed with the so-cooled reaction mass of a), and wherein temperature in b) is in the range of about 40 to about 150° C.

17. A process according to claim 14 wherein the reaction mass formed in a) is cooled or allowed to cool to a temperature in the range of about 50 to about 180° C., and wherein said conjugated diene hydrocarbon is mixed with the reaction mass of a) while said reaction mass is at a temperature of at least about 50° C., so that the reaction mass of b) is formed without applying additional heat while conducting b).

18. A process according to claim 14 wherein the reaction mass formed in a) is cooled or allowed to cool to a temperature in the range of about 20 to about 80° C., wherein said conjugated diene hydrocarbon is mixed with the so-cooled reaction mass of a), and wherein the resultant mixture is heated to a temperature in the range of about 50 to about 150° C.

19. A process according to claim 14 wherein in b) said conjugated diene hydrocarbon is added to said reaction mass from a).

20. A process according to claim 14 wherein in b) said conjugated diene hydrocarbon and maleic anhydride are added to said reaction mass from a).

21. A process according to claim 14 wherein a) and b) are conducted in the same reaction vessel without removing the reaction mass of a) from said reaction vessel.

22. A process according to claim 14 wherein a) is conducted for a period of time sufficient to achieve a conversion of maleic anhydride to alkenyl succinic anhydride in the range of about 50 to about 95 mole % and then b) is carried out.

23. A process according to any of claims 14–22 wherein the olefin used in a) contains in the range of about 8 to about 14 carbon atoms in the molecule and wherein the diene hydrocarbon used in b) contains in the range of about 4 to about 8 carbon atoms in the molecule.

24. A process which comprises:

a) heating a mixture formed from maleic anhydride and a stoichiometric excess of olefin consisting essentially of at least one $C_{12}$ branched olefin and/or at least one internal linear olefin at a temperature in the range of about 180 to about 280° C. to form a reaction mass containing a liquid phase, said liquid phase comprising at least one $C_{12}$ alkenyl succinic anhydride, residual maleic anhydride, and $C_{12}$ branched and/or internal linear olefin; and b) mixing with reaction mass from a) at least one conjugated diene hydrocarbon having in the range of 4 to about 6 carbon atoms in an amount at least stoichiometrically equivalent to the amount of residual maleic anhydride present in said reaction mass from a), and thereafter having the temperature of the resultant mixture in the range of about 40 to about 150° C. to form a reaction mass comprising at least tetrahydrophthalic anhydride and/or alkyl-substituted tetrahydrophthalic anhydride, and at least one $C_{12}$ alkenyl succinic anhydride.

25. A process according to claim 24 further comprising recovering from the reaction mass of b), a product consisting essentially of tetrahydrophthalic anhydride and/or alkyl-substituted tetrahydrophthalic anhydride, and at least one $C_{12}$ alkenyl succinic anhydride.

26. A process according to claim 24 wherein the reaction mass formed in a) is cooled or allowed to cool to a temperature in the range of about 40 to about 150° C., wherein said conjugated diene hydrocarbon is mixed with the so-cooled reaction mass of a), and wherein temperature in b) is in the range of about 40 to about 110° C.

27. A process according to claim 24 wherein the reaction mass formed in a) is cooled or allowed to cool to a temperature in the range of about 50 to about 150° C., and wherein said conjugated diene hydrocarbon is mixed with the reaction mass of a) while said reaction mass is at a temperature of at least about 50° C., so that the reaction mass of b) is formed without applying additional heat while conducting b).

28. A process according to claim 24 wherein the reaction mass formed in a) is cooled or allowed to cool to a temperature in the range of about 40 to about 100° C., wherein said conjugated diene hydrocarbon is mixed with the so-cooled reaction mass of a), and wherein the resultant mixture is heated to a temperature in the range of about 50 to about 150° C.

29. A process according to claim 24 wherein a) and b) are conducted in the same reaction vessel without removing the reaction mass of a) from said reaction vessel.

30. A process according to claim 24 wherein the temperature in a) is maintained in the range of about 190 to about 260° C., and wherein a) is conducted for a period of time sufficient to achieve a conversion of maleic anhydride to alkenyl succinic anhydride in the range of about 50 to about 95 mole % and then b) is carried out.

31. A process according to claim 24, 29 or 30 wherein the olefin used in a) consists essentially of $C_{12}$ branched olefin derived from propylene tetramer, and wherein the conjugated diene hydrocarbon used in b) consists essentially of butadiene, isoprene, or piperylene, or a mixture of at least two of them.

* * * * *